United States Patent [19]

Förster et al.

[11] Patent Number: 4,481,365

[45] Date of Patent: Nov. 6, 1984

[54] TRIFLUOROMETHYL-PHENOXY-PHENYL-SILICON DERIVATIVES, PROCESSES FOR THEIR PREPARATION, AND THEIR USE AS HERBICIDES AND PLANT-GROWTH REGULATORS

[75] Inventors: Heinz Förster, Wuppertal; Ludwig Eue, Leverkusen; Robert Schmidt; Klaus Lürssen, both of Bergisch-Gladbach, all of Fed. Rep. of Germany

[73] Assignee: Bayer Aktiengesellschaft, Leverkusen, Fed. Rep. of Germany

[21] Appl. No.: 433,923

[22] Filed: Oct. 12, 1982

[30] Foreign Application Priority Data

Oct. 22, 1981 [DE] Fed. Rep. of Germany ....... 3141860

[51] Int. Cl.$^3$ .............................. C07F 7/08; C07F 7/10; E05B 65/00; E05B 63/00
[52] U.S. Cl. .................................. 556/422; 556/447; 556/440; 556/416; 556/423; 556/429; 556/413; 71/94; 71/95; 71/88; 71/98; 71/105; 71/106; 71/107; 71/121; 71/124; 71/125; 546/14; 544/69; 548/406; 260/239 B
[58] Field of Search ............... 556/422, 447, 440, 416, 556/423, 429, 413; 546/14; 544/69; 548/406; 260/239 B; 71/94, 95, 88, 98, 105, 106, 107, 121, 124, 125

[56] References Cited

U.S. PATENT DOCUMENTS

| | | | |
|---|---|---|---|
| 3,328,449 | 6/1967 | Haluska | 556/422 X |
| 3,576,021 | 4/1971 | Grindahl | 556/422 X |
| 3,770,790 | 11/1973 | Clark | 556/447 UX |
| 4,045,459 | 8/1977 | Foery et al. | 556/422 X |

FOREIGN PATENT DOCUMENTS 2215629 10/1973 Fed. Rep. of Germany ...... 556/440 UX

*Primary Examiner*—Paul F. Shaver
*Attorney, Agent, or Firm*—Sprung Horn Kramer & Woods

[57] ABSTRACT

A trifluoromethyl-phenoxy-phenyl-silicon compound is disclosed of the general formula

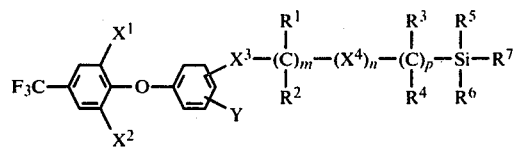

in which
X$^1$ and X$^2$ independently of each other represent a hydrogen, fluorine, chlorine, bromine or iodine atom,
Y represents a hydrogen or halogen atom or a cyano or nitro group,
n is 0 or 1,
m is 0, 1, 2 or 3,
p is 0, 1, 2 or 3,
X$^3$ and X$^4$ independently of each other represent oxygen or a —CO—O— group,
R$^1$, R$^2$, R$^3$ and R$^4$ independently of one another represent a hydrogen atom or a C$_1$ to C$_5$ alkyl group,
R$^5$ and R$^6$ independently of each other represent a C$_1$ to C$_5$ alkyl group, and
R$^7$ represents a C$_1$ to C$_5$ alkyl or hydroxyl group, a chlorine, bromine, or iodine atom or a C$_2$ to C$_5$ alkenoxy, C$_2$ to C$_5$ alkinoxy,
C$_1$ to C$_5$ alkylthio, C$_2$ to C$_5$ alkenyl-thio or C$_2$ to C$_5$ alkinyl-thio group or a C$_1$ to C$_5$ alkoxy group which is straight-chain or branched and optionally substituted by fluorine, chlorine, bromine, iodine, C$_1$ to C$_5$ alkoxy and/or C$_1$ to C$_5$ alkylthio, or represents a radical of the general formula

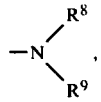

wherein
R$^8$ and R$^9$ independently of each other represent a phenyl radical which is optionally substituted by fluorine, bromine, and/or iodine, or represent a straight-chain or branched C$_1$ to C$_5$ alkyl, C$_2$ to C$_5$ alkenyl or C$_2$ to C$_5$ alkinyl group,
or wherein
R$^8$ and R$^9$, together with the nitrogen atom to which they are bonded, represent a pyrrolidyl radical which is optionally substituted by methyl and/or ethyl, represent a morpholinyl radical which is optionally substituted by methyl, or represent an azacycloheptyl, piperidyl, 3-methyl-piperidyl, 4-methyl-piperidyl, 2-ethyl-piperidyl, 4-ethyl-piperidyl, 2,3-dimethyl-piperidyl, 2,4-dimethyl-piperidyl, 2,5-dimethyl-piperidyl, or 3,5-dimethyl-piperidyl radical.

The trifluoromethyl-phenoxy-phenyl-silicon compounds are useful as herbicides and plant growth regulators. Disclosed are compositions containing the same and methods for their preparation.

17 Claims, No Drawings

4,481,365

TRIFLUOROMETHYL-PHENOXY-PHENYL-SILICON DERIVATIVES, PROCESSES FOR THEIR PREPARATION, AND THEIR USE AS HERBICIDES AND PLANT-GROWTH REGULATORS

The invention relates to certain new trifluoromethyl-phenoxy-phenyl-silicon derivatives, to several processes for their production, and to their use as herbicides and plant-growth regulators.

It is already known that certain substituted diphenyl ethers can be used for combating weeds (see (German Offenlegungsschrift No. 2,311,638). Thus, for example, sodium 5-(2-chlorotrifluoromethyl-phenoxy)-2-nitrobenzoate can be used for combating weeds. The herbicidal action of this substance is good, but the selectivity is not always adequate.

The present invention now provides, as new compounds the trifluoromethyl-phenoxy-phenyl-silicon derivatives of the formula

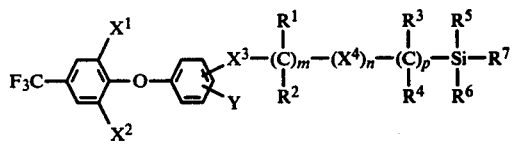

in which
X$^1$ and X$^2$ independently of each other represent a hydrogen, fluorine, chlorine, bromine or iodine atom,
Y represents a hydrogen or halogen atom or a cyano or nitro group,
n is 0 or 1,
m is 0, 1, 2 or 3,
p is 0, 1, 2 or 3,
X$^3$ and X$^4$ independently of each other represent oxygen or a —CO—O— group,
R$^1$, R$^2$, R$^3$ and R$^4$ independently of one another represent a hydrogen atom or a C$_1$ to C$_5$ alkyl group,
R$^5$ and R$^6$ independently of each other represent a C$_1$ to C$_5$ alkyl group, and
R$^7$ represents a C$_1$ to C$_5$ alkyl or hydroxyl group, a chlorine, bromine or iodine atom, a C$_2$ to C$_5$ alkenoxy, C$_2$ to C$_5$ alkinoxy, C$_1$ to C$_5$ alkylthio, C$_2$ to C$_5$ alkenylthio, C$_2$ to C$_5$ alkinylthio group or a C$_1$ to C$_5$ alkoxy group which is straight-chain or branched and is optionally substituted by fluorine, chlorine, bromine, iodine, C$_1$ to C$_5$ alkoxy and/or C$_1$ to C$_5$ alkylthio, or represents a radical of the general formula

wherein
R$^8$ and R$^9$ independently of each other represent a phenyl radical which is optionally substituted by fluorine, chlorine, bromine and/or iodine, or represent a straight-chain or branched C$_1$ to C$_5$ alkyl, C$_2$ to C$_5$ alkenyl or C$_2$ to C$_5$ alkinyl group,
or wherein
R$^8$ and R$^9$, together with the nitrogen atom to which they are bonded, represent a pyrrolidyl radical which is optionally substituted by methyl and/or ethyl, represent a morpholinyl radical which is optionally substituted by methyl, or represent an zacycloheptyl, piperidyl, 3-methyl-piperidyl, 4-methyl-piperidyl, 2-ethyl-piperidyl, 4-ethyl-piperidyl, 2,3-dimethyl-piperidyl, 2,4-dimethyl-piperidyl, 2,5-dimethyl-piperidyl or 3,5-dimethyl-piperidyl radical.

According to the present invention we further provide a process for the production of a compound of the present invention characterised in that (a) a diphenyl ether of the general formula

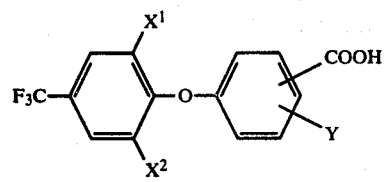

in which
X$^1$, X$^2$ and Y have the meanings given above, is reacted with a compound of the general formula

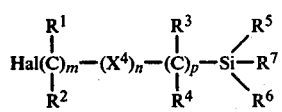

in which
X$^4$, R$^1$, R$^2$, R$^3$, R$^4$, R$^5$, R$^6$, R$^7$, m, n and p have the meanings given above and Hal represents a chlorine or bromine atom,
if desired in the presence of an acid acceptor and, if desired, in the presence of a diluent, or (b) a diphenyl ether derivative of the general formula

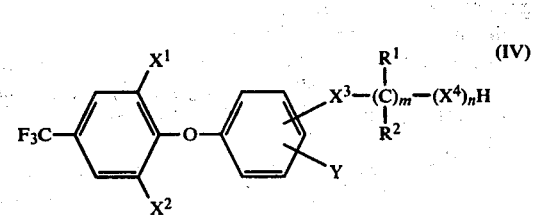

in which
X$^1$, X$^2$, X$^3$, X$^4$, Y, R$^1$, R$^2$, m and n have the meanings given above,
is reacted with a silicon derivative of the general formula

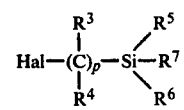

in which
R$^3$, R$^4$, R$^5$, R$^6$, R$^7$, p and Hal have the meanings given above,
if desired in the presence of an acid acceptor and, if desired, in the presence of a diluent, or (c) a trifluoromethyl-phenoxy-phenyl-silicon derivative of the general formula

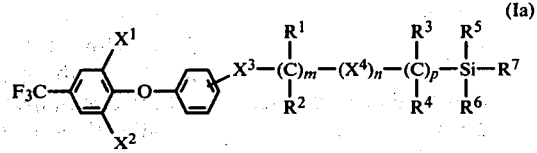

in which
X¹, X², X³, X⁴, R¹, R², R³, R⁵, R⁶, R⁷, m, n and p have the meanings given above,
is reacted with nitric acid, if desired in the presence of a catalyst and, if desired, in the presence of a diluent, or (d) a trifluoromethyl-phenoxy-phenyl-silicon derivative of the general formula

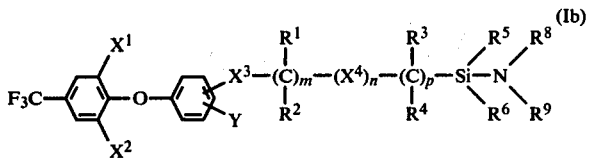

in which
X¹, X², X³, X⁴, Y, R¹, R², R³, R⁴, R⁵, R⁶, R⁸, R⁹, m, n and p have the meanings given above,
is reacted with a hydroxy compound of the general formula

HO—R¹⁰     (VI)

in which
R¹⁰ represents a hydrogen atom, or a $C_2$ to $C_5$ alkenyl, $C_2$ to $C_5$ alkinyl or $C_1$ to $C_5$ alkyl group which is straight-chain or branched and optionally substituted by fluorine, chlorine, bromine and/or iodine, if desired in the presence of a diluent, Finally, it has been found that the new trifluoromethylphenoxy-phenyl-silicon derivatives of the formula (I) are distinguished by outstanding herbicidal and plant growth-regulating properties.

Surprisingly, the trifluoromethyl-phenoxy-phenyl-silicon derivatives according to the present invention, of the formula (I), possess a substantially better herbicidal activity than sodium 5-(2-chloro-4-trifluoromethyl-phenoxy)-2-nitrobenzoate, which is a structurally similar, previously known active compound with the same direction of action. In addition, the substances according to the invention can, against expectations, also be employed for regulating plant growth.

Preferred trifluoromethyl-phenoxy-phenyl-silicon derivatives according to the present invention are those, in which X¹ and X² independently of each other represent a hydrogen or chlorine atom,
Y represents a hydrogen or chlorine atom or a cyano or nitro group,
m is 0, 1, 2 or 3,
n is 0 or 1,
p is 0, 1, 2 or 3,
X³ and X⁴ independently of each other represent oxygen or a —CO—O— group,
R¹, R², R³ and R⁴ independently of one another represent a hydrogen atom or a methyl or ethyl group,
R⁵ and R⁶ independently of each other represent a methyl, ethyl, n-propyl, iso-propyl, n-, iso-, sec.- or tert.-butyl group, and
R⁷ represents a methyl, ethyl, n-propyl, iso-propyl, n-, iso-, sec.- or tert.-butyl, or hydroxyl group, a chlorine atom or a methoxy, ethoxy, n-propoxy, iso-propoxy, n-butoxy, iso-butoxy, sec.-butoxy, tert.-butoxy, methylthio, ethylthio, propenoxy, propinyloxy, propenylthio or propinylthio group which is optionally substituted by fluorine, chlorine, methoxy, ethoxy, methylthio and/or ethylthio, or represents a radical of the general formula

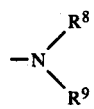

wherein
R⁸ and R⁹ independently of each other represent an optionally fluorine-substituted and/or chlorine-substituted phenyl, methyl, ethyl, n-propyl, isopropyl, n-, iso-, sec.- or tert.-butyl, prop-2-enyl, but-2-enyl, prop-2-inyl or but-2-inyl group,
or wherein
R⁸ and R⁹, together with the nitrogen atom to which they are bonded, represent a pyrrolidyl radical which is optionally substituted by methyl and/or ethyl, represent a morpholinyl radical which is optionally substituted by methyl, or represent an aza-cycloheptyl, piperidyl, 3-methyl-piperidyl, 4-methyl-piperidyl, 2-ethyl-piperidyl, 4-ethyl-piperidyl, 2,3-dimethyl-piperidyl, 2,4-dimethyl-piperidyl, 2,5-dimethyl-piperidyl or 3,5-dimethyl-piperidyl radical.

The compounds of formula (I) listed in Table 1 below may be mentioned individually as examples of compounds according to the present invention.

TABLE 1

| X¹ | X² | X³ | X⁴ | Y | R¹ | R² | R³ | R⁴ | R⁵ | R⁶ | R⁷ | m | n | p |
|---|---|---|---|---|---|---|---|---|---|---|---|---|---|---|
| H | H | 3-CO₂— | | 4-NO₂ | H | H | | | CH₃ | CH₃ | CH₃ | 1 | 0 | 0 |
| H | H | 3-CO₂— | | 4-NO₂ | H | H | | | CH₃ | CH₃ | CH₃ | 1 | 0 | 0 |
| H | Cl | 3-CO₂— | | 4-NO₂ | H | H | | | CH₃ | CH₃ | —N(CH₃)₂ | 1 | 0 | 0 |
| Cl | Cl | 3-CO₂— | | 4-NO₂ | H | H | | | CH₃ | CH₃ | —N(CH₃)₂ | 1 | 0 | 0 |

TABLE 1-continued $$\text{F}_3\text{C}-\underset{X^2}{\underset{|}{\overset{X^1}{\overset{|}{\bigcirc}}}}-\text{O}-\underset{Y}{\bigcirc}-X^3-(\overset{R^1}{\underset{R^2}{C}})_m-(X^4)_n-(\overset{R^3}{\underset{R^4}{C}})_p-\underset{R^6}{\overset{R^5}{\underset{|}{Si}}}-R^7 \quad (I)$$

| X¹ | X² | X³ | X⁴ | Y | R¹ | R² | R³ | R⁴ | R⁵ | R⁶ | R⁷ | m | n | p |
|---|---|---|---|---|---|---|---|---|---|---|---|---|---|---|
| Cl | H | 3-CO₂— | | 4-NO₂ | H | H | | | CH₃ | CH₃ | —N⟨piperidinyl⟩ | 1 | 0 | 0 |
| Cl | H | 3-CO₂— | | 4-NO₂ | H | H | | | CH₃ | CH₃ | —N⟨morpholinyl⟩ | 1 | 0 | 0 |
| Cl | H | 3-CO₂— | | 4-NO₂ | H | H | | | CH₃ | CH₃ | —N⟨hexamethyleneimino⟩ | 1 | 0 | 0 |
| Cl | H | 3-CO₂— | | 4-NO₂ | H | H | | | CH₃ | CH₃ | —N(CH₂—CH=CH₂)₂ | 1 | 0 | 0 |
| Cl | H | 3-CO₂— | | 4-NO₂ | H | H | | | CH₃ | CH₃ | —OH | 1 | 0 | 0 |
| H | H | 3-CO₂— | | 4-NO₂ | H | H | | | CH₃ | CH₃ | —OH | 1 | 0 | 0 |
| Cl | Cl | 3-CO₂— | | 4-NO₂ | H | H | | | CH₃ | CH₃ | —OH | 1 | 0 | 0 |
| Cl | Cl | 3-CO₂— | | 4-NO₂ | H | H | | | CH₃ | CH₃ | —OCH₃ | 1 | 0 | 0 |
| H | Cl | 3-CO₂ | | 4-NO₂ | H | H | | | CH₃ | CH₃ | —OCH₃ | 1 | 0 | 0 |
| H | H | 3-CO₂— | | 4-NO₂ | H | H | | | CH₃ | CH₃ | —OCH₃ | 1 | 0 | 0 |
| H | H | 3-CO₂— | | 4-NO₂ | H | H | | | CH₃ | CH₃ | —O—iso-C₃H₇ | 1 | 0 | 0 |
| H | Cl | 3-CO₂— | | 4-NO₂ | H | H | | | CH₃ | CH₃ | —O—iso-C₃H₇ | 1 | 0 | 0 |
| Cl | Cl | 3-CO₂— | | 4-NO₂ | H | H | | | CH₃ | CH₃ | —O—iso-C₃H₇ | 1 | 0 | 0 |
| Cl | H | 3-CO₂— | | 4-NO₂ | H | H | | | CH₃ | CH₃ | —OC₂H₅ | 1 | 0 | 0 |
| Cl | H | 3-CO₂— | | 4-NO₂ | H | H | | | CH₃ | CH₃ | —OCH₂CF₃ | 1 | 0 | 0 |
| Cl | H | 3-CO₂— | | 4-NO₂ | H | H | | | CH₃ | CH₃ | —O—n-C₄H₉ | 1 | 0 | 0 |
| Cl | H | 3-CO₂— | | 4-NO₂ | H | H | | | CH₃ | CH₃ | —N(CH₃)(phenyl) | 1 | 0 | 0 |
| Cl | H | 3-O | —CO₂— | 4-NO₂ | CH₃ | H | H | H | CH₃ | CH₃ | —N(CH₃)(phenyl) | 1 | 1 | 1 |
| Cl | H | 3-O | —CO₂— | 4-NO₂ | CH₃ | H | H | H | CH₃ | CH₃ | CH₃ | 1 | 1 | 1 |
| H | H | 3-O | —CO₂— | 4-NO₂ | CH₃ | H | H | H | CH₃ | CH₃ | CH₃ | 1 | 1 | 1 |
| H | H | 3-O | —CO₂— | 4-NO₂ | CH₃ | H | H | H | CH₃ | CH₃ | —N(CH₃)₂ | 1 | 1 | 1 |
| H | Cl | 3-O | —CO₂— | 4-NO₂ | CH₃ | H | H | H | CH₃ | CH₃ | —N(CH₃)₂ | 1 | 1 | 1 |
| Cl | Cl | 3-O | —CO₂— | 4-NO₂ | CH₃ | H | H | H | CH₃ | CH₃ | —N(CH₃)₂ | 1 | 1 | 1 |
| Cl | H | 3-O— | —CO₂— | 4-NO₂ | CH₃ | H | H | H | CH₃ | CH₃ | —N⟨piperidinyl⟩ | 1 | 1 | 1 |
| Cl | H | 3-O— | —CO₂— | 4-NO₂ | CH₃ | H | H | H | CH₃ | CH₃ | —N⟨morpholinyl⟩ | 1 | 1 | 1 |
| Cl | H | 3-O— | —CO₂— | 4-NO₂ | CH₃ | H | H | H | CH₃ | CH₃ | —N⟨hexamethyleneimino⟩ | 1 | 1 | 1 |
| Cl | Cl | 3-O— | —CO₂— | 4-NO₂ | CH₃ | H | H | H | CH₃ | CH₃ | —N(CH₂—CH=CH₂)₂ | 1 | 1 | 1 |

TABLE 1-continued $$\text{(I)}\quad F_3C-\underset{\underset{X^2}{|}}{\overset{\overset{X^1}{|}}{\bigcirc}}-O-\underset{Y}{\bigcirc}-X^3-(\overset{\overset{R^1}{|}}{\underset{\underset{R^2}{|}}{C}})_m-(X^4)_n-(\overset{\overset{R^3}{|}}{\underset{\underset{R^4}{|}}{C}})_p-\overset{\overset{R^5}{|}}{\underset{\underset{R^6}{|}}{Si}}-R^7$$

| $X^1$ | $X^2$ | $X^3$ | $X^4$ | Y | $R^1$ | $R^2$ | $R^3$ | $R^4$ | $R^5$ | $R^6$ | $R^7$ | m | n | p |
|---|---|---|---|---|---|---|---|---|---|---|---|---|---|---|
| Cl | H | 3-O— | —CO$_2$— | 4-NO$_2$ | CH$_3$ | H | H | H | CH$_3$ | CH$_3$ | —OH | 1 | 1 | 1 |
| H | H | 3-O— | —CO$_2$— | 4-NO$_2$ | CH$_3$ | H | H | H | CH$_3$ | CH$_3$ | —OH | 1 | 1 | 1 |
| Cl | Cl | 3-O— | —CO$_2$— | 4-NO$_2$ | CH$_3$ | H | H | H | CH$_3$ | CH$_3$ | —OH | 1 | 1 | 1 |
| Cl | H | 3-O— | —CO$_2$— | 4-NO$_2$ | CH$_3$ | H | H | H | CH$_3$ | CH$_3$ | —OCH$_3$ | 1 | 1 | 1 |
| H | H | 3-O— | —CO$_2$— | 4-NO$_2$ | CH$_3$ | H | H | H | CH$_3$ | CH$_3$ | —OCH$_3$ | 1 | 1 | 1 |
| Cl | Cl | 3-O— | —CO$_2$— | 4-NO$_2$ | CH$_3$ | H | H | H | CH$_3$ | CH$_3$ | —OCH$_3$ | 1 | 1 | 1 |
| Cl | H | 3-O— | —CO$_2$ | 4-NO$_2$ | CH$_3$ | H | H | H | CH$_3$ | CH$_3$ | —OCH$_2$CF$_3$ | 1 | 1 | 1 |
| Cl | H | 3-O— | —CO$_2$— | 4-NO$_2$ | CH$_3$ | H | H | H | CH$_3$ | CH$_3$ | —OC$_2$H$_5$ | 1 | 1 | 1 |
| Cl | Cl | 3-O— | —CO$_2$— | 4-NO$_2$ | CH$_3$ | H | H | H | CH$_3$ | CH$_3$ | O—iso-C$_3$H$_7$ | 1 | 1 | 1 |
| H | Cl | 3-O— | —CO$_2$ | 4-NO$_2$ | CH$_3$ | H | H | H | CH$_3$ | CH$_3$ | O—iso-C$_3$H$_7$ | 1 | 1 | 1 |
| H | H | 3-O | —CO$_2$— | 4-NO$_2$ | CH$_3$ | H | H | H | CH$_3$ | CH$_3$ | O—iso-C$_3$H$_7$ | 1 | 1 | 1 |
| Cl | H | 3-O | —CO$_2$— | 4-NO$_2$ | CH$_3$— | H | H | H | CH$_3$ | CH$_3$ | O—n-C$_4$H$_9$ | 1 | 1 | 1 |
| H | H | 3-O | | 4-NO$_2$ | H | | | H | CH$_3$ | CH$_3$ | —CH$_3$ | 1 | 0 | 0 |
| H | H | 3-O | | 4-NO$_2$ | H | | | H | CH$_3$ | CH$_3$ | —N(CH$_3$)$_2$ | 1 | 0 | 0 |
| H | Cl | 3-O | | 4-NO$_2$ | H | | | H | CH$_3$ | CH$_3$ | —N(CH$_3$)$_2$ | 1 | 0 | 0 |
| Cl | Cl | 3-O | | 4-NO$_2$ | H | | | H | CH$_3$ | CH$_3$ | —N(CH$_3$)$_2$ | 1 | 0 | 0 |
| Cl | H | 3-O | | 4-NO$_2$ | H | | | H | CH$_3$ | CH$_3$ | —N(piperidinyl) | 1 | 0 | 0 |
| Cl | H | 3-O | | 4-NO$_2$ | H | | | H | CH$_3$ | CH$_3$ | —N(morpholinyl) | 1 | 0 | 0 |
| Cl | H | 3-O | | 4-NO$_2$ | H | | | H | CH$_3$ | CH$_3$ | —N(piperidinyl) | 1 | 0 | 0 |
| Cl | H | 3-O | | 4-NO$_2$ | H | | | H | CH$_3$ | CH$_3$ | —N(CH$_2$—CH=CH$_2$)$_2$ | 1 | 0 | 0 |
| Cl | H | 3-O | | 4-NO$_2$ | H | | | H | CH$_3$ | CH$_3$ | —N(C$_6$H$_5$)(CH$_3$) | 1 | 0 | 0 |
| Cl | H | 3-O | | 4-NO$_2$ | H | | | H | CH$_3$ | CH$_3$ | —OH | 1 | 0 | 0 |
| Cl | Cl | 3-O | | 4-NO$_2$ | H | | | H | CH$_3$ | CH$_3$ | —OH | 1 | 0 | 0 |
| H | H | 3-O | | 4-NO$_2$ | H | | | H | CH$_3$ | CH$_3$ | —OH | 1 | 0 | 0 |
| H | H | 3-O | | 4-NO$_2$ | H | | | H | CH$_3$ | CH$_3$ | —OCH$_3$ | 1 | 0 | 0 |
| H | Cl | 3-O | | 4-NO$_2$ | H | | | H | CH$_3$ | CH$_3$ | —OCH$_3$ | 1 | 0 | 0 |
| Cl | Cl | 3-O | | 4-NO$_2$ | H | | | H | CH$_3$ | CH$_3$ | —OCH$_3$ | 1 | 0 | 0 |
| Cl | H | 3-O | | 4-NO$_2$ | H | | | H | CH$_3$ | CH$_3$ | —OC$_2$H$_5$ | 1 | 0 | 0 |
| Cl | H | 3-O | | 4-NO$_2$ | H | | | H | CH$_3$ | CH$_3$ | —OCH$_2$CF$_3$ | 1 | 0 | 0 |
| Cl | H | 3-O | | 4-NO$_2$ | H | | | H | CH$_3$ | CH$_3$ | —iso-C$_3$H$_7$ | 1 | 0 | 0 |
| Cl | Cl | 3-O | | 4-NO$_2$ | H | | | H | CH$_3$ | CH$_3$ | —O—iso-C$_3$H$_7$ | 1 | 0 | 0 |
| H | H | 3-O | | 4-NO$_2$ | H | | | H | CH$_3$ | CH$_3$ | —O—iso-C$_3$H$_7$ | 1 | 0 | 0 |
| Cl | H | 3-O | | 4-NO$_2$ | H | | | H | CH$_3$ | CH$_3$ | —O—n-C$_4$H$_9$ | 1 | 0 | 0 |
| Cl | H | 4-CO$_2$— | | H | H | | | H | CH$_3$ | CH$_3$ | CH$_3$ | 1 | 0 | 0 |
| Cl | Cl | 3-CO$_2$— | | H | H | | | H | CH$_3$ | CH$_3$ | CH$_3$ | 1 | 0 | 0 |
| Cl | Cl | 4-CO$_2$— | | H | H | | | H | CH$_3$ | CH$_3$ | CH$_3$ | 1 | 0 | 0 |
| Cl | H | 3-CO$_2$— | | H | H | | | H | CH$_3$ | CH$_3$ | CH$_3$ | 1 | 0 | 0 |
| Cl | H | 3-O | | H | H | | | H | CH$_3$ | CH$_3$ | CH$_3$ | 1 | 0 | 0 |
| Cl | H | 4-O | | H | H | | | H | CH$_3$ | CH$_3$ | CH$_3$ | 1 | 0 | 0 |
| Cl | Cl | 3-O | —CO$_2$— | H | CH$_3$ | H | H | H | CH$_3$ | CH$_3$ | CH$_3$ | 1 | 1 | 1 |
| Cl | Cl | 4-O | —CO$_2$— | H | CH$_3$ | H | H | H | CH$_3$ | CH$_3$ | CH$_3$ | 1 | 1 | 1 |
| Cl | Cl | 3-O | | H | H | | H | | CH$_3$ | CH$_3$ | CH$_3$ | 1 | 0 | 0 |
| Cl | Cl | 4-O | | H | H | | | | CH$_3$ | CH$_3$ | CH$_3$ | 1 | 0 | 0 |

If 5-(2,6-dichloro-4-trifluoromethyl-phenoxy)-2-nitrobenzoic acid and chloromethyltrimethylsilane are used as starting materials, the course of reaction variant (a) according to the present invention is illustrated by the following equation:

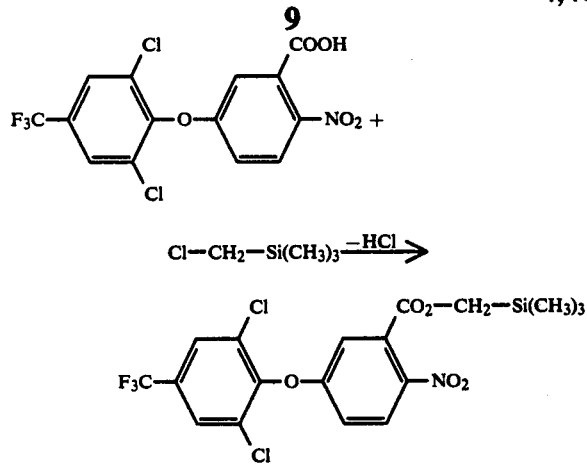

If 2-(5-(2-chloro-4-trifluoromethyl-phenoxy)-2-nitrophenoxy)-acetic acid and chloromethyl-trimethylsilane are used as starting materials, the course of reaction variant (b) according to the present invention is illustrated by the following equation:

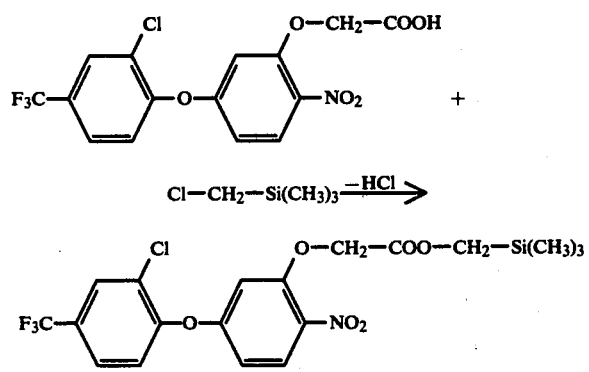

If trimethylsilyl-methyl 2-(5-(2-chloro-4-trifluoromethyl-phenoxy)-2-nitrophenoxy)-acetate and nitric acid are used as starting materials, the course of reaction variant (c) according to the present invention is illustrated by the following equation:

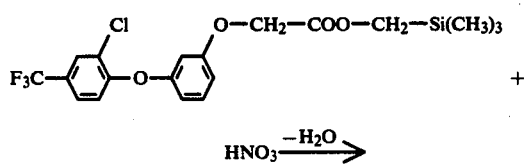

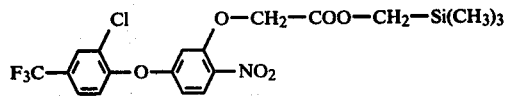

If dimethylamino-dimethyl-sylyl-methyl 5-(2-chloro-4-trifluoromethyl-phenoxy)-2-nitro-benzoate and methanol are used as starting materials, the course of reaction variant (d) according to the present invention is illustrated by the following equation:

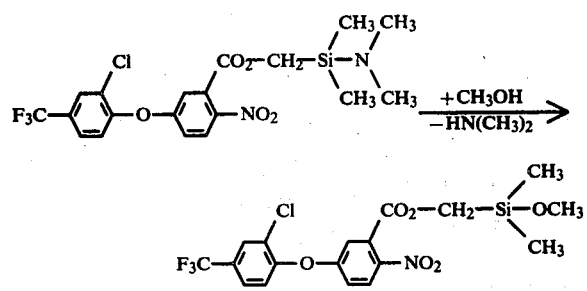

Preferred ethers of formula (II) required as starting materials in carrying out reaction variant (a) according to the invention are those in which $X^1$, $X^2$ and Y have those meanings which have already been mentioned for these radicals in connection with the description of the preferred compounds according to the invention, of the formula (I).

The 5-(2-chloro-4-trifluoromethyl-phenoxy) and the 5-(2,6-dichloro-4-trifluoromethyl-phenoxy) derivatives of 2-nitro-benzoic acid, 2-cyano-benzoic acid, 2-chlorobenzoic acid and benzoic acid may be mentioned as examples.

The compounds of the formula (II) are already known, or can be prepared in a simple manner according to customary methods (see German Offenlegungsschrift No. 2,311,638, British No. 2,058,055 and U.S. Pat. No. 4,031,131).

Preferred compounds of formula (II) furthermore required as starting materials in reaction variant (a) according to the invention are those in which $R^1$, $R^2$, $R^3$ $R^4$, $R^5$, $R^6$, $R^7$, $X^4$, m, n and p have those meanings which have already been respectively mentioned in connection with the description of the preferred compounds according to the present invention, and Hal represents a chlorine or bromine atom.

The following may be mentioned individually as examples of compounds of the formula (III):

TABLE 2

| $R^1$ | $R^2$ | $R^3$ | $R^4$ | $R^5$ | $R^7$ | $R^6$ | m | n | p | $X^4$ |
|---|---|---|---|---|---|---|---|---|---|---|
|  |  | H | H | $CH_3$ | $CH_3$ | $CH_3$ | 0 | 0 | 1 |  |
| H | $CH_3$ | H | H | $CH_3$ | $CH_3$ | $CH_3$ | 1 | 1 | 1 | $CO_2$ |
|  |  | H | H | $CH_3$ | $N(CH_3)_2$ | $CH_3$ | 0 | 0 | 1 |  |
|  |  | H | H | $CH_3$ | (N H ring) | $CH_3$ | 0 | 0 | 1 |  |

TABLE 2-continued $$\text{Hal}(C)_m-(X^4)_n-(C)-Si-R^6 \quad \text{(III)}$$

with substituents $R^1, R^2$ on first C; $R^3, R^4$ on second C; $R^5, R^7$ on Si.

Hal = chlorine or bromine

| $R^1$ | $R^2$ | $R^3$ | $R^4$ | $R^5$ | $R^7$ | $R^6$ | m | n | p | $X^4$ |
|---|---|---|---|---|---|---|---|---|---|---|
| | | H | H | $CH_3$ | (N-H, O ring) | $CH_3$ | 0 | 0 | 1 | |
| | | H | H | $CH_3$ | (N-H ring) | $CH_3$ | 0 | 0 | 1 | |
| | | H | H | $CH_3$ | OH | $CH_3$ | 0 | 0 | 1 | |
| | | H | H | $CH_3$ | $OCH_3$ | $CH_3$ | 0 | 0 | 1 | |
| | | H | H | $CH_3$ | $OCH_2CF_3$ | $CH_3$ | 0 | 0 | 1 | |
| | | H | H | $CH_3$ | $-O-iso-C_3H_7$ | $CH_3$ | 0 | 0 | 1 | |
| | | H | H | $CH_3$ | $-O-n-C_4H_9$ | $CH_3$ | 0 | 0 | 1 | |
| H | $CH_3$ | H | H | $CH_3$ | $N(CH_3)_2$ | $CH_3$ | 1 | 1 | 1 | $CO_2$ |
| H | $CH_3$ | H | H | $CH_3$ | (N-H ring) | $CH_3$ | 1 | 1 | 1 | $CO_2$ |
| H | $CH_3$ | H | H | $CH_3$ | (N-H, O ring) | $CH_3$ | 1 | 1 | 1 | $CO_2$ |
| H | $CH_3$ | H | H | $CH_3$ | (N-H ring) | $CH_3$ | 1 | 1 | 1 | $CO_2$ |
| | | H | H | $CH_3$ | $N(CH_2-CH=CH_2)_2$ | $CH_3$ | 0 | 0 | 1 | |
| H | $CH_3$ | H | H | $CH_3$ | $N(CH_2-CH=CH_2)_2$ | $CH_3$ | 1 | 1 | 1 | $CO_2$ |
| H | $CH_3$ | H | H | $CH_3$ | OH | $CH_3$ | 1 | 1 | 1 | $CO_2$ |
| H | $CH_3$ | H | H | $CH_3$ | $OCH_3$ | $CH_3$ | 1 | 1 | 1 | $CO_2$ |
| H | $CH_3$ | H | H | $CH_3$ | $OCH_2CF_3$ | $CH_3$ | 1 | 1 | 1 | $CO_2$ |
| H | $CH_3$ | H | H | $CH_3$ | $O-iso-C_3H_7$ | $CH_3$ | 1 | 1 | 1 | $CO_2$ |
| H | $CH_3$ | H | H | $CH_3$ | $O-n-C_4H_9$ | $CH_3$ | 1 | 1 | 1 | $CO_2$ |
| | | H | H | $CH_3$ | $OC_2H_5$ | $CH_3$ | 0 | 0 | 1 | |
| H | $CH_3$ | H | H | $CH_3$ | $OC_2H_5$ | $CH_3$ | 1 | 1 | 1 | $CO_2$ |
| H | $CH_3$ | H | H | $CH_3$ | $-N(CH_3)-C_6H_5$ | $CH_3$ | 1 | 1 | 1 | $CO_2$ |

The compounds of the formula (III) are known, or can be prepared in a simple manner according to customary methods (see Houben-Weyl, volume 13/5, page 39 et seq., Georg Thieme-Verlag, Stuttgart-New York). According to this, trimethyl-silyl-methyl 2-bromopropionate is prepared by reacting 2-bromopropionic acid and iodo-trimethylsilyl-methane in the presence of diluents, for example, acetone, and in the presence of bases, for example, di-aza-bicycloundecene, at the boiling point of the solvent.

Reaction variant (a) according to the invention is preferably carried out in the presence of an acid acceptor. Any of the customary acid-binding agents can be used as the acid acceptor. Alkali metal hydroxides (such as sodium hydroxide and potassium hydroxide), alkali metal carbonates and alcoholates (such as sodium carbonate and potassium carbonate, and sodium and potassium methylate or ethylate), and aliphatic, aromatic or hetero-cyclic amines (for example triethylamine, trimethylamine, dimethylaniline, dimethylbenzylamine, pyridine, diazabicyclooctane, diazabicyclononene and diazabicycloundecene) are preferred.

Virtually any of the inert organic solvents can be used as diluents in carrying out reaction variant (a) according to the invention. Aliphatic and aromatic, optionally halogenated hydrocarbons (such as pentane, hexane, heptane, cyclohexane, petroleum ether, petrol, ligroin, benzene, toluene, xylene, methylene chloride, ethylene chloride, chloroform, carbon tetrachloride, chlorobenzene and o-dichlorobenzene), ethers (such as diethyl ether and dibutyl ether, glycol dimethyl ether and diglycol dimethyl ether, tetrahydrofuran and dioxane), ketones (such as acetone, methyl ethyl ketone, methyl isopropyl ketone and methyl isobutyl ketone), esters (such as methyl acetate and ether acetate), and furthermore nitriles (such as acetonitrile and propionitrile), amides (such as dimethylformamide, dimethylacetamide and N-methyl-pyrrolidone) and strongly polar solvents (such as dimethylsulphoxide, tetramethylenesulphone and hexamethylphosphoric acid triamide) are preferred.

In carrying out reaction variant (a) according to the invention, the reaction temperatures can be varied within a relatively wide range. In general, the reaction is carried out at a temperature between $-20°$ and $+150°$ C., preferably between $-10°$ and $+120°$ C.

Reaction variant (a) according to the invention is carried out in general under normal pressure.

In carrying out reaction variant (a) according to the invention, the starting materials of the formulae (II) and (III) are employed in general in about equimolar amounts. An excess of one or other of the components is possible. The reaction is carried out in general in a suitable diluent in the presence of an acid acceptor, and the reaction mixture is stirred for several hours at the required temperature. The working-up is effected according to customary methods. In general the procedure is carried out in the following manner: after the end of the reaction, an organic solvent, for example toluene, is added, and the organic phase, in the customary manner, is washed, dried and concentrated by distilling off the solvent.

Some of the new compounds are obtained in the form of oils, which in some cases cannot be distilled without decomposition, but can be freed from the last volatile constituents by so-called "incipient distillation", that is to say by prolonged heating to moderately elevated temperature under reduced pressure, and can be purified in this manner. The new substances are characterised by their refractive index. If the new products are obtained in solid form, they can be purified by recrystallisation. They are then characterised by their melting point.

Preferred diphenyl ether derivatives of formula (IV) required as starting materials in reaction variant (b) according to the invention are those in which $X^1$, $X^2$, $X^3$, $X^4$, Y, $R^1$, $R^2$, m and n have those meanings which have already been respectively mentioned in connection with the description of the preferred compounds according to the present invention.

The following may be mentioned individually as examples of compounds of formula (IV):

TABLE 3

$$F_3C-\text{(Ar)}-O-\text{(Ar)}-X^3-(C)_m-(X^4)_nH \quad (IV)$$

with substituents $X^1, X^2$ on first ring, $Y$ and $R^1, R^2$ on the carbon chain.

| $X^1$ | $X^2$ | $X^3$ | $X^4$ | Y | $R^1$ | $R^2$ | m | n |
|---|---|---|---|---|---|---|---|---|
| Cl | Cl | O | $CO_2$ | $NO_2$ | H | $CH_3$ | 1 | 1 |
| H | Cl | O | $CO_2$ | $NO_2$ | H | $CH_3$ | 1 | 1 |
| H | Cl | $CO_2$ | | $NO_2$ | | | 0 | 0 |
| Cl | Cl | | $NO_2$ | | | | 0 | 0 |
| Cl | Cl | $CO_2$ | | H | | | 0 | 0 |
| H | Cl | $CO_2$ | | H | | | 0 | 0 |
| H | Cl | O | $CO_2$ | H | H | $CH_3$ | 1 | 1 |
| Cl | Cl | O | $CO_2$ | H | H | $CH_3$ | 1 | 1 |
| Cl | H | O | | $NO_2$ | | | 0 | 0 |
| Cl | Cl | O | $NO_2$ | | | | 0 | 0 |
| Cl | H | O | | H | | | 0 | 0 |

TABLE 3-continued $$F_3C-\text{(Ar)}-O-\text{(Ar)}-X^3-(C)_m-(X^4)_nH \quad (IV)$$

| $X^1$ | $X^2$ | $X^3$ | $X^4$ | Y | $R^1$ | $R^2$ | m | n |
|---|---|---|---|---|---|---|---|---|
| Cl | Cl | O | | H | | | 0 | 0 |

The compounds of the formula (IV) are known, or can be prepared in a simple manner according to customary methods (see German Auslegeschrift No. 2,304,006, European Published Patent Application No. 28,277 and British No. 2,058,055).

Preferred compounds of formula (V) furthermore required as starting materials in reaction variants (b) according to the invention are those in which $R^3$, $R^4$, $R^5$, $R^6$, $R^7$ and p have those meanings which have already been respectively mentioned in connection with the description of the preferred compounds according to the present invention.

The following may be mentioned individually as examples of compounds of the formula (V):

TABLE 4

$$\text{Hal}-(C)_p-Si\begin{smallmatrix}R^3 & R^5 \\ | & / \\ | & \backslash \\ R^4 & R^6\end{smallmatrix}-R^7$$

| $R^3$ | $R^4$ | $R^5$ | $R^7$ | $R^6$ | p | Hal |
|---|---|---|---|---|---|---|
| H | H | $CH_3$ | $CH_3$ | $CH_3$ | 1 | Cl(Br) |
| H | H | $CH_3$ | $N(CH_3)_2$ | $CH_3$ | 1 | Cl(Br) |
| H | H | $CH_3$ | (piperidinyl N-H) | $CH_3$ | 1 | Cl(Br) |
| H | H | $CH_3$ | (morpholinyl N-H-O) | $CH_3$ | 1 | Cl(Br) |
| H | H | $CH_3$ | (piperidinyl N-H) | $CH_3$ | 1 | Cl(Br) |
| H | H | $CH_3$ | OH | $CH_3$ | 1 | Cl(Br) |
| H | H | $CH_3$ | $OCH_3$ | $CH_3$ | 1 | Cl(Br) |
| H | H | $CH_3$ | $OCH_2CF_3$ | $CH_3$ | 1 | Cl(Br) |
| H | H | $CH_3$ | $OC_3H_7$—iso | $CH_3$ | 1 | Cl(Br) |
| H | H | $CH_3$ | $OC_4H_9$—n | $CH_3$ | 1 | Cl(Br) |
| H | H | $CH_3$ | $OC_2H_5$ | $CH_3$ | 1 | Cl(Br) |
| H | H | $CH_3$ | $N(CH_2-CH=CH_2)_2$ | $CH_3$ | 1 | Cl(Br) |
| H | H | $CH_3$ | $-N(CH_3)-\text{Ph}$ | $CH_3$ | 1 | Cl(Br) |

The compounds of the formula (V) are known, or can be prepared in a simple manner according to customary methods (see Houben-Weyl, volume 13/5, page 39 et seq., Georg Thieme Verlag, Stuttgart-New York).

Any of the customary acid-binding agents can be used as acid acceptors in reaction variant (b) according to the invention. Preferred acid-binding agents are any of those which have been mentioned in connection with the description of reaction variant (a) according to the invention.

Virtually any of the inert organic solvents can be used as diluents in carrying out reaction variant (b) according to the invention. Preferred diluents are those which have been mentioned in connection with the description of reaction variant (a) according to the invention.

In carrying out reaction variant (b) according to the invention, the reaction temperatures can be varied within a relatively wide range. In general, the reaction is carried out at a temperature between $-20°$ and $+120°$ C., preferably between $-10°$ and $+80°$ C.

Reaction variant (b) according to the invention is carried out in general under normal pressure.

In carrying out reaction variant (b) according to the invention, the starting materials of the formulae (IV) and (V) are employed in general in about equimolar amounts. An excess of one or other of the components is possible. The reaction is carried out in general in a suitable diluent in the presence of an acid acceptor, and the reaction mixture is stirred for several hours at the required temperature. The working-up is effected according to customary methods. In general, the procedure is carried out in the following manner: after the end of the reaction, an organic solvent, for example toluene, is added, and the organic phase, in the customary manner, is washed, dried, and concentrated by distilling off the solvent.

Some of the new compounds are obtained in the form of oils, which in some cases cannot be distilled without decomposition, but can be freed from the last volatile constituents by so-called "incipient distillation", that is to say by prolonged heating to moderately elevated temperatures under reduced pressure, and can be purified in this manner.

The new substances are characterised by their refractive index. If the new products are obtained in solid form, they can be purified by recrystallisation. They are then characterised by their melting point.

Preferred trifluoromethyl-phenoxy-phenyl-silicon derivative of formula (Ia) to be employed as starting materials in reaction variant (c) are those in which $X^1$, $X^2$, $X^3$, $X^4$, $R^1$ $R^2$, $R^3$, $R^4$, $R^5$, $R^6$, $R^7$, m, n and p have those meanings which have already been respectively mentioned in connection with the description of the preferred compounds according to the present invention.

The substances listed as formulae in Table 5 below may be mentioned as examples of compounds of the formula (Ia).

TABLE 5

(Ia)

$F_3C$—[phenyl with $X^1$, $X^2$]—O—[phenyl]—$X^3$—$(C)_m$—$(X^4)_n$—$(C)_p$—$Si$—$R^7$ with substituents $R^1$, $R^2$ on first C, $R^3$, $R^4$ on $(X^4)$, $R^5$, $R^6$ on second C

| $X^1$ | $X^2$ | $X^3$ | $X^4$ | $R^1$ | $R^2$ | $R^3$ | $R^4$ | $R^5$ | $R^6$ | $R^7$ | m | n | p |
|---|---|---|---|---|---|---|---|---|---|---|---|---|---|
| H | Cl | 3-$CO_2$— | | | | H | H | $CH_3$ | $CH_3$ | —$CH_3$ | 1 | 0 | 0 |
| Cl | Cl | 3-$CO_2$— | | | | H | H | $CH_3$ | $CH_3$ | —$CH_3$ | 1 | 0 | 0 |
| H | H | 3-$CO_2$— | | | | H | H | $CH_3$ | $CH_3$ | —$CH_3$ | 1 | 0 | 0 |
| Cl | H | 3-$CO_2$— | | | | H | H | $CH_3$ | $CH_3$ | —N(phenyl)($CH_3$) | 1 | 0 | 0 |
| H | H | 3-$CO_2$— | | | | H | H | $CH_3$ | $CH_3$ | —$N(CH_3)_2$ | 1 | 0 | 0 |
| H | Cl | 3-$CO_2$— | | | | H | H | $CH_3$ | $CH_3$ | —$N(CH_3)_2$ | 1 | 0 | 0 |
| Cl | Cl | 3-$CO_2$— | | | | H | H | $CH_3$ | $CH_3$ | —$N(CH_3)_2$ | 1 | 0 | 0 |
| Cl | H | 3-$CO_2$— | | | | H | H | $CH_3$ | $CH_3$ | —N(piperidinyl) | 1 | 0 | 0 |
| Cl | H | 3-$CO_2$— | | | | H | H | $CH_3$ | $CH_3$ | —N(morpholinyl) | 1 | 0 | 0 |
| Cl | H | 3-$CO_2$— | | | | H | H | $CH_3$ | $CH_3$ | —N(hexamethyleneimino) | 1 | 0 | 0 |
| Cl | H | 3-$CO_2$— | | | | H | H | $CH_3$ | $CH_3$ | —$N(CH_2-CH=CH_2)_2$ | 1 | 0 | 0 |
| Cl | H | 3-$CO_2$— | | | | H | H | $CH_3$ | $CH_3$ | —$OCH_3$ | 1 | 0 | 0 |
| Cl | Cl | 3-$CO_2$— | | | | H | H | $CH_3$ | $CH_3$ | —$OCH_3$ | 1 | 0 | 0 |

TABLE 5-continued

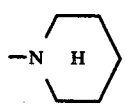

(Ia)

| X¹ | X² | X³ | X⁴ | R¹ | R² | R³ | R⁴ | R⁵ | R⁶ | R⁷ | m | n | p |
|---|---|---|---|---|---|---|---|---|---|---|---|---|---|
| Cl | H | 3-CO₂— |  | H | H |  |  | CH₃ | CH₃ | —OC₂H₅ | 1 | 0 | 0 |
| Cl | H | 3-CO₂— |  | H | H |  |  | CH₃ | CH₃ | —OCH₂CF₃ | 1 | 0 | 0 |
| Cl | H | 3-CO₂— |  | H | H |  |  | CH₃ | CH₃ | —O—iso-C₃H₇ | 1 | 0 | 0 |
| Cl | H | 3-CO₂— |  | H | H |  |  | CH₃ | CH₃ | —O—n-C₄H₉ | 1 | 0 | 0 |
| Cl | Cl | 3-O | CO₂ | CH₃ | H | H | H | CH₃ | CH₃ | —CH₃ | 1 | 1 | 1 |
| Cl | H | 3-O | CO₂ | CH₃ | H | H | H | CH₃ | CH₃ | —CH₃ | 1 | 1 | 1 |
| H | H | 3-O | CO₂ | CH₃ | H | H | H | CH₃ | CH₃ | —CH₃ | 1 | 1 | 1 |
| H | H | 3-O | CO₂ | CH₃ | H | H | H | CH₃ | CH₃ | —N(CH₃)₂ | 1 | 1 | 1 |
| H | Cl | 3-O | CO₂ | CH₃ | H | H | H | CH₃ | CH₃ | —N(CH₃)₂ | 1 | 1 | 1 |
| Cl | Cl | 3-O | CO₂ | CH₃ | H | H | H | CH₃ | CH₃ | —N(CH₃)₂ | 1 | 1 | 1 |
| Cl | H | 3-O | CO₂ | CH₃ | H | H | H | CH₃ | CH₃ | 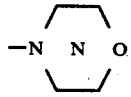 | 1 | 1 | 1 |
| Cl | H | 3-O | CO₂ | CH₃ | H | H | H | CH₃ | CH₃ | 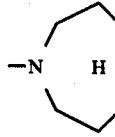 | 1 | 1 | 1 |
| Cl | H | 3-O | CO₂ | CH₃ | H | H | H | CH₃ | CH₃ | 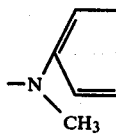 | 1 | 1 | 1 |
| Cl | H | 3-O | CO₂ | CH₃ | H | H | H | CH₃ | CH₃ | —N(CH₂—CH=CH₂)₂ | 1 | 1 | 1 |
| Cl | H | 3-O | CO₂ | CH₃ | H | H | H | CH₃ | CH₃ | 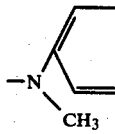 | 1 | 1 | 1 |
| Cl | H | 3-CO₂ | CO₂ | CH₃ | H | H | H | CH₃ | CH₃ | 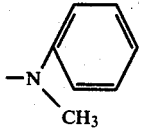 | 1 | 1 | 1 |
| Cl | H | 3-CO₂ | CO₂ | CH₃ | H | H | H | CH₃ | CH₃ | 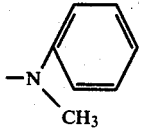 | 1 | 1 | 1 |
| Cl | H | 3-O— | CO₂ | CH₃ | H | H | H | CH₃ | CH₃ | —OCH₃ | 1 | 1 | 1- |
| Cl | Cl | 3-O— | CO₂ | CH₃ | H | H | H | CH₃ | CH₃ | —OCH₃ | 1 | 1 | 1 |
| Cl | H | 3-O— | CO₂ | CH₃ | H | H | H | CH₃ | CH₃ | —OCH₂CF₃ | 1 | 1 | 1 |
| Cl | H | 3-O— | CO₂ | CH₃ | H | H | H | CH₃ | CH₃ | —OC₂H₅ | 1 | 1 | 1 |
| Cl | H | 3-O— | CO₂ | CH₃ | H | H | H | CH₃ | CH₃ | —O—iso-C₃H₇ | 1 | 1 | 1 |
| Cl | H | 3-O— | CO₂ | CH₃ | H | H | H | CH₃ | CH₃ | —O—n-C₄H₉ | 1 | 1 | 1 |
| Cl | H | 3-O— |  | H | H |  |  | CH₃ | CH₃ | —CH₃ | 1 | 0 | 0 |
| Cl | Cl | 3-O— |  | H | H |  |  | CH₃ | CH₃ | —CH₃ | 1 | 0 | 0 |
| H | H | 3-O— |  | H | H |  |  | CH₃ | CH₃ | —CH₃ | 1 | 0 | 0 |
| H | H | 3-O— |  | H | H |  |  | CH₃ | CH₃ | —N(CH₃)₂ | 1 | 0 | 0 |
| H | Cl | 3-O— |  | H | H |  |  | CH₃ | CH₃ | —N(CH₃)₂ | 1 | 0 | 0 |
| Cl | Cl | 3-O— |  | H | H |  |  | CH₃ | CH₃ | —N(CH₃)₂ | 1 | 0 | 0 |

TABLE 5-continued $$F_3C-\text{[Ar]}(X^1)(X^2)-O-\text{[Ar]}-X^3-(C)_m(R^1)(R^2)-(X^4)_n-(C)_p(R^3)(R^4)-Si(R^5)(R^6)-R^7 \quad (Ia)$$

| X¹ | X² | X³ | X⁴ | R¹ | R² | R³ | R⁴ | R⁵ | R⁶ | R⁷ | m | n | p |
|----|----|----|----|----|----|----|----|----|----|----|---|---|---|
| Cl | H | 3-O— | | H | H | | | CH₃ | CH₃ | —N(piperidinyl) | 1 | 0 | 0 |
| Cl | H | 3-O— | | H | H | | | CH₃ | CH₃ | —N(morpholinyl) | 1 | 0 | 0 |
| Cl | H | 3-O— | | H | H | | | CH₃ | CH₃ | —N(hexamethyleneimino) | 1 | 0 | 0 |
| Cl | H | 3-O— | | H | H | | | CH₃ | CH₃ | —N(CH₂—CH=CH₂)₂ | 1 | 0 | 0 |
| Cl | H | 3-O— | | H | H | | | CH₃ | CH₃ | —OCH₃ | 1 | 0 | 0 |
| Cl | H | 3-O— | | H | H | | | CH₃ | CH₃ | —N(CH₃)(C₆H₅) | 1 | 0 | 0 |
| Cl | Cl | 3-O— | | H | H | | | CH₃ | CH₃ | —OCH₃ | 1 | 0 | 0 |
| Cl | H | 3-O— | | H | H | | | CH₃ | CH₃ | —OC₂H₅ | 1 | 0 | 0 |
| Cl | H | 3-O— | | H | H | | | CH₃ | CH₃ | —OCH₂CF₃ | 1 | 0 | 0 |
| Cl | H | 3-O— | | H | H | | | CH₃ | CH₃ | —O—iso-C₃H₇ | 1 | 0 | 0 |
| Cl | H | 3-O— | | H | H | | | CH₃ | CH₃ | —O—n-C₄H₉ | 1 | 0 | 0 |

In the case of reaction variant (c) according to the invention, concentrated nitric acid is used in general for nitration.

The trifluoromethyl-phenoxy-phenyl-silicon derivatives of the formula (Ia) which are required as starting materials in reaction variant (c) according to the invention are new: however, they can be prepared in a simple manner by reaction variant (a) and (b) according to the invention.

Reaction variant (c) according to the invention is carried out using a diluent, if desired. Preferred diluents in this process are halogenated hydrocarbons, such as, for example, methylene chloride.

Reaction variant (c) according to the invention is carried out in the presence of a catalyst, if desired. Preferred catalysts are protonic acids, such as sulphuric acid or acetic acid.

In reaction variant (c), the reaction temperature is kept in general between −20° and +80° C., preferably between 0° and 50° C. Reaction variant (c) is carried out in general under normal pressure.

To carry out process (c) according to the invention in general 0.9 to 2 mol, preferably 1.0 to 1.3 mol, of nitric acid and, if appropriate, about the same amount of a catalyst are employed per mol of the compound of the formula (Ia). The starting components are preferably combined while cooling with ice, and then stirred, if appropriate at a slightly elevated temperature, until the end of the reaction.

The working-up is effected according to customary methods. In general, the procedure is carried out in the following manner: after the end of the reaction the reaction mixture is poured into ice-water, the mixture is filtered under suction, and the product obtained is purified, if required, by recrystallisation.

Preferred trifluoromethyl-phenoxyphenyl-silicon derivatives of formula (Ib) required as starting materials in reaction variant (d) according to the invention are those in which $X^1$, $X^2$, $X^3$, $X^4$, Y, $R^1$, $R^2$, $R^3$, $R^4$, $R^5$, $R^6$, $R^8$, $R^9$, m, n and p have those meanings which have already been respectively mentioned in connection with the description of preferred compounds according to the invention.

The following may be mentioned individually as examples of the compounds of the formula (Ib):

TABLE 6:

$$\text{(Ib)}$$

Structure: F3C-substituted phenyl with X1, X2 substituents, linked via O to a phenyl bearing Y and X3—(C(R1)(R2))m—(X4)n—(C(R3)(R4))p—Si(R5)(R6)—N(R8)(R9)

| X1 | X2 | X3 | X4 | Y | R1 | R2 | R3 | R4 | R5 | R6 | R8 | R9 | m | n | p |
|---|---|---|---|---|---|---|---|---|---|---|---|---|---|---|---|
| H | H | CO2 | | NO2 | | | H | H | CH3 | CH3 | CH3 | CH3 | 0 | 0 | 1 |
| H | Cl | CO2 | | NO2 | | | H | H | CH3 | CH3 | CH3 | CH3 | 0 | 0 | 1 |
| Cl | H | CO2 | | NO2 | | | H | H | CH3 | CH3 | CH3 | phenyl | 0 | 0 | 1 |
| Cl | Cl | CO2 | | NO2 | | | H | H | CH3 | CH3 | CH3 | CH3 | 0 | 0 | 1 |
| Cl | H | CO2 | | NO2 | | | H | H | CH3 | CH3 | | —(CH2)5— | 0 | 0 | 1 |
| Cl | H | CO2 | | NO2 | | | H | H | CH3 | CH3 | | —(CH2)2—O—(CH2)2 | 0 | 0 | 1 |
| Cl | H | CO2 | | NO2 | | | H | H | CH3 | CH3 | | —(CH2)6— | 0 | 0 | 1 |
| Cl | H | CO2 | | NO2 | | | H | H | CH3 | CH3 | CH—CH=CH2 | CH—CH—CH2 | 0 | 0 | 1 |
| Cl | H | O | CO2 | NO2 | H | CH3 | H | CH3 | CH3 | CH3 | | phenyl | 1 | 1 | 1 |
| H | H | O | CO2 | NO2 | H | CH3 | H | CH3 | CH3 | CH3 | CH3 | CH3 | 1 | 1 | 1 |
| H | Cl | O | CO2 | NO2 | H | CH3 | H | CH3 | CH3 | CH3 | CH3 | CH3 | 1 | 1 | 1 |
| Cl | Cl | O | CO2 | NO2 | H | CH3 | H | CH3 | CH3 | CH3 | CH3 | CH3 | 1 | 1 | 1 |
| Cl | H | O | CO2 | NO2 | H | CH3 | H | CH3 | CH3 | | —(CH2)5 | 1 | 1 | 1 |
| Cl | H | O | CO2 | NO2 | H | CH3 | H | CH3 | CH3 | | —(CH2)2—O—(CH2)2— | 1 | 1 | 1 |
| Cl | H | O | CO2 | NO2 | H | CH3 | H | CH3 | CH3 | | —(CH2)6— | 1 | 1 | 1 |
| Cl | H | O | CO2 | NO2 | H | CH3 | H | CH3 | CH3 | CH2—CH=CH2 | CH—CH=CH2 | 1 | 1 | 1 |
| H | H | O | | NO2 | | | H | H | CH3 | CH3 | CH3 | CH3 | 0 | 0 | 1 |
| H | Cl | O | | NO2 | | | H | H | CH3 | CH3 | CH3 | CH3 | 0 | 0 | 1 |
| Cl | Cl | O | | NO2 | | | H | H | CH3 | CH3 | CH3 | CH3 | 0 | 0 | 1 |
| Cl | H | O | | NO2 | | | H | H | CH3 | CH3 | | —(CH2)5— | 0 | 0 | 1 |
| Cl | H | O | | NO2 | | | H | H | CH3 | CH3 | | —(CH2)2—O—(CH2)2— | 0 | 0 | 1 |
| Cl | H | O | | NO2 | | | H | H | CH3 | CH3 | | —(CH2)6— | 0 | 0 | 1 |
| Cl | H | O | | NO2 | | | H | H | CH3 | CH3 | CH2—CH=CH2 | CH2—CH=CH2 | 0 | 0 | 1 |
| Cl | H | O | | NO2 | | | H | N | CH3 | CH3 | CH3 | phenyl | 0 | 0 | 1 |
| Cl | H | CO2 | CO2 | NO2 | H | CH3 | H | CH3 | CH3 | CH3 | CH3 | naphthyl | 1 | | 1 |
| H | H | CO2 | CO2 | NO2 | H | CH3 | H | CH3 | CH3 | CH3 | CH3 | CH3 | 1 | 1 | 1 |
| H | Cl | CO2 | CO2 | NO2 | H | CH3 | H | CH3 | CH3 | CH3 | CH3 | CH3 | 1 | 1 | 1 |
| Cl | Cl | CO2 | CO2 | NO2 | H | CH3 | H | CH3 | CH3 | CH3 | CH3 | CH3 | 1 | 1 | 1 |
| Cl | H | CO2 | CO2 | NO2 | H | CH3 | H | CH3 | CH3 | | —(CH2)5— | 1 | 1 | 1 |
| Cl | H | CO2 | CO2 | NO2 | H | CH3 | H | CH3 | CH3 | | —(CH2)2—O—(CH2)2— | 1 | 1 | 1 |
| Cl | H | CO2 | CO2 | NO2 | H | CH3 | H | CH3 | CH3 | | —(CH2)6— | 1 | 1 | 1 |
| Cl | H | CO2 | CO2 | NO2 | H | CH3 | H | CH3 | CH3 | CH2—CH=CH2 | CH2—CH=CH2 | 1 | 1 | 1 |

The compounds of the formula (Ib) are new: however, they can be prepared in a simple manner by reaction variant (a), (b) and (c) according to the invention.

The following may be mentioned individually as examples of the further starting materials of the formula (IV): water, methanol, ethanol, n-propanol, isopropanol, butan-1-ol, butan-2-ol, 2-methyl-propan-2-ol and 2-methyl-propan-3-ol.

Reaction variant (d) according to the invention is carried out using a diluent, if appropriate. The compounds of the formula (VI) are preferably used as diluents in this process.

In reaction variant (d), the reaction temperature is kept in general between 0° and 150° C.; the reaction is preferably carried out at between 0° C. and 120° C. Reaction variant (d) is carried out in general under normal pressure.

To carry out reaction variant (d) according to the invention, up to 10 mol of the compound of the formula (VI) are employed per mol of the compound of the formula (Ib). The working-up is effected according to customary methods.

The active compounds according to the invention influence plant growth and can therefore be used as defoliants, desiccants, agents for destroying broad-leaved plants, germination inhibitors and, especially, as weed-killers. By "weeds" in the broadest sense there are meant plants growing in places where they are not desired.

Whether the compounds according to the invention act as total herbicides or selective herbwicides depends essentially on the amount used.

The active compounds according to the present invention may be used, for example, to combat the following plants:

dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Rorippa, Rotala, Lindernia, Lamium, Veronica, Abutilon, Emex, Datura, Viola, Galeopsis, Papaver, Centaurea and Solanum; and monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

The active compounds according to the present invention may be used, for example, as selective herbicides in the following cultures:

dicotyledon cultures of the genera Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita; and monocotyledon cultures of the genera Oryza, Zea, Triticum, Hordeum, Avena, Secale, Sorghum, Panicum, Saccharum, Ananas, Asparagus and Allium.

However, the use of the active compounds according to the invention is in no way restricted to these genera but also embraces other plants, in the same way.

Depending on the concentrations, the compounds can be used for the total combating of weeds, for example on industrial terrain and railway tracks and on paths and squares with or without trees. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cacao plantations, soft fruit plantings and hopfields, and for the selective combating of weeds in annual cultures.

The active compounds according to the invention are particularly suitable for selectively combating weeds in various important cultures, such as cereals and soya beans.

In addition, the active compounds according to the invention possess a very good plant growth-regulating activity. They are particularly suitable for inhibiting growth, and for the defoliation and desiccation of the leaves in cotton.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations may be produced in known manner, for example by mixing the active compounds with extenders, that is to say liquid or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention, as such or in the form of their formulations, can also be used as mixtures with known herbicides or plant-growth regulators, for combating weeds or as plant-growth regulators, respectively, finished formulations or tank mixing being possible. Mixtures with other known active compounds, such as fungicides, insecticides, acaricides, nematicides, bird repellants, growth factors, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomising or scattering.

When used as herbicides, the active compounds according to the invention can be applied either before or after emergence of the plants. They are preferably applied after emergence of the plants, that is to say by the post-emergence method. They can also be incorporated into the soil before sowing.

The amount of active compound used can vary within a substantial range. It depends essentially on the nature of the desired effect. In general, the amounts used are between 0.01 and 50 kg of active compound per hectare of soil area, preferably between 0.05 and 10 kg per ha.

The present invention also provides a method of combating weeds which comprises applying to the weeds, or to a habitat thereof, a compound of the present invention alone or in the form of a composition containing as active ingredient a compound of the present invention in admixture with a diluent or carrier.

The present invention also provides a method of regulating the growth of plants which comprises applying to the plants, or to a habitat thereof, a compound of the present invention alone or in the form of a composition containing as active ingredient a compound of the present invention in admixture with a diluent or carrier.

The present invention further provides crops protected from damage by weeds by being grown in areas in which immediately prior to and/or during the time of the growing a compound of the present invention was applied alone or in admixture with a diluent or carrier.

The present invention further provides plants, the growth of which has been regulated by their being grown in areas in which immediately prior to and/or during the time of the growing a compound of the present invention was applied alone or in admixture with a diluent or carrier.

It will be seen that the usual methods of providing a harvested crop may be improved by the present invention.

The preparation and the use of the active compounds according to the invention are evident from the Examples which follow.

PREPARATIVE EXAMPLES

Example 1

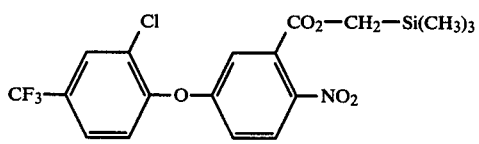

18.1 g (0.05 mol) of 5-(2-chloro-4-trifluoromethyl-phenoxy)-2-nitro-benzoic acid are dissolved in 100 ml of dimethylsulphoxide. 9.8 g of diazabicycloundecane are added at 20° C., while cooling. The mixture is stirred for a further half hour. 7.4 g (0.06 mol) of chloromethyl-trimethylsilane are then added dropwise at 20° C., and the mixture is heated at 100° C. for 20 hours. The reaction mixture is thereafter concentrated, and the residue is taken up in toluene. The organic phase is washed successively with dilute hydrochloric acid, aqueous sodium hydroxide solution and water, and is then dried and evaporated down. The residue is dissolved in ligroin, the solution is stirred under active charcoal, the latter is filtered off under suction over kieselguhr, and the filtrate is then concentrated. 20 g (89% of theory) of trimethyl-silyl-methyl 5-(2-chloro-4-trifluoromethyl-phenoxy)-2-nitro-benzoate are obtained as a viscous oil.

EXAMPLE 2

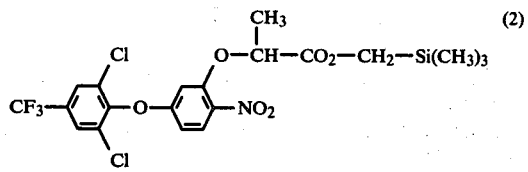

16.8 g (0.11 mol) of diazabicycloundecane are added dropwise to 40 g (0.09 mol) of 2-(5-(2,6-dichloro-4-trifluoromethyl-phenoxy)-2-nitro-phenoxy)-propionic acid and 100 g of acetone at 20° C., whilst cooling. 13.8 g (0.11 mol) of chloromethyl-trimethylsilane are then added dropwise at 20° C. The reaction mixture is stirred for 20 hours at 50° C. and is then concentrated, and 300 ml of water are added. The pH value is adjusted to 5 by the addition of glacial acetic acid, the mixture is extracted with toluene, and the organic phase is concentrated. 39.5 g (83% of theory) of trimethylsilylmethyl 2-(5-2,6-dichloro-4-trifluoromethyl-phenoxy)-2-nitro-phenoxy)-propionate are obtained as an oil of refractive index $n_D^{20}$: 1.5325.

EXAMPLE 3

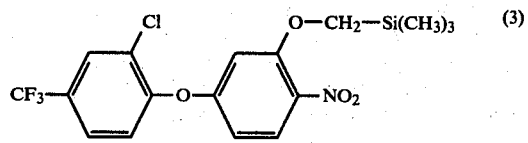

18.7 g of diazabicycloundecene are added dropwise to 33.3 g (0.1 mol) of 5-(2-chloro-4-trifluoromethyl-phenoxy)-2-nitrophenol and 150 ml of dimethylsulphoxide at 20° C., whilst cooling. 15.1 g (0.123 mol) of chloromethyl-trimethylsilane are added dropwise, and the reaction mixture is heated at 100° C. for 6 hours. The reaction mixture is then concentrated. The residue which remains is taken up in toluene. The organic phase is washed successively with dilute hydrochloric acid, aqueous sodium hydroxide solution and water, and is dried and concentrated. 22.2 g (53% of theory) of 5-(2-chlorotrifluoromethyl-phenoxy-2-nitro-phenoxy)-methyl-trimethylsilane are obtained as a yellow oil of refractive index $n_D^{20}$: 1.5368.

The compounds of the formula (I) which are listed in Table 7 below are prepared analogously to Example 1, 2 or 3:

TABLE 7

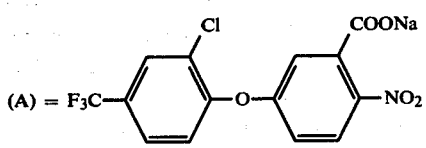

| Example No. | X¹ | X² | X³ | X⁴ | Y | R¹ | R² | R³ | R⁴ | R⁵ | R⁶ | R⁷ | m | n | p | Melting point [°C.] |
|---|---|---|---|---|---|---|---|---|---|---|---|---|---|---|---|---|
| 4 | Cl | Cl | 3-CO₂— | | 4-NO₂ | H | H | | | CH₃ | CH₃ | CH₃ | 1 | 0 | 0 | 61 |
| 5 | Cl | Cl | 3-O— | | 4-NO₂ | H | H | | | CH₃ | CH₃ | CH₃ | 1 | 0 | 0 | 78–79 |

The herbicidal and plant growth regulating activity of the compounds of this invention is illustrated by the following biotest Examples.

In these Examples, the compounds according to the present invention are each identified by the number (given in brackets) of the corresponding preparative Example.

The known comparison compound is identified as follows:

(A) = $F_3C$—⟨Cl⟩—O—⟨COONa, NO₂⟩

Sodium 5-(2-chloro-4-trifluoromethyl-phenoxy)-2-nitrobenzoate (disclosed in German Offenlegungsschrift No. 2,311,638 or U.S. Pat. No. 4,063,929).

Example A

Post Emergence Test
Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

Test plants which had a height of 5 to 15 m were sprayed with the preparation of the active compound in such a way as to apply the particular amount of active compound desired per unit area. The concentration of the spray liquor was so chosen that the particular amount of active compound desired was applied in 2,000 liters of water/ha. After three weeks, the degree of damage to the plants was rated in % damage in comparison to the development of the untreated control. The figures denoted:

0%=no action (like untreated control)
100%=total destruction

In this test, the active compounds (1), (2), (3) and (4) showed a better selective herbicidal activity than the comparative substance (A).

Example B

Defoliation and desiccation of the leaves of cotton

Solvent: 30 parts by weight of dimethylformamide
Emulsifier: 1 part by weight of polyoxyethylene sorbitane monolaurate To produce a suitable preparation of active compound, 1 part by weight of active compound was mixed with the stated amounts of solvent and emulsifier and the mixture was made up to the desired concentration with water.

Cotton plants were grown in a greenhouse until the 5th secondary leaf had unfolded completely. In this stage, the plants were sprayed with the preparations of active compound until dripping wet. After 1 week, the shedding of leaves and the desiccation of the leaves were rated, in comparison with the control plants.

The figures of merit had the following meanings:
0 denoted no desiccation of the leaves, no shedding of leaves
+ denoted slight desiccation of the leaves, slight shedding of leaves
+ + denoted severe desiccation of the leaves, severe shedding of leaves
+ + + denoted very severe desiccation of the leaves, very severe shedding of leaves.

In this test, the active compounds (1), (2), (3) and (4) showed a powerful to very powerful activity.

It will be understood that the specification and examples are illustrative, but not limitative of the present invention and that other embodiments within the spirit and scope of the invention will suggest themselves to those skilled in the art.

What is claimed is:

1. A trifluoromethyl-phenoxy-phenyl-silicon compound of the general formula

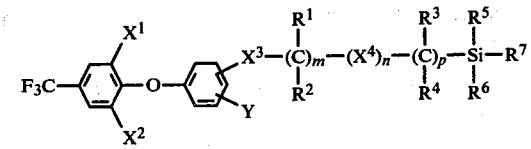

in which
X¹ and X² independently of each other represent a hydrogen, fluorine, chlorine, bromine or iodine atom,
Y represents a hydrogen or halogen atom or a cyano or nitro group,
n is 0 or 1,
m is 0, 1, 2 or 3,
p is 0, 1, 2 or 3,
X³ and X⁴ independently of each other represent oxygen or a —CO—O— group,
R¹, R², R³ and R⁴ independently of one another represent a hydrogen atom or a $C_1$ to $C_5$ alkyl group,
R⁵ and R⁶ independently of each other represent a $C_1$ to $C_5$ alkyl group, and $R^7$ represents a $C_1$ to $C_5$ alkyl or hydroxyl group, a chlorine, bromine, or iodine atom or a $C_2$ to $C_5$ alkenoxy, $C_2$ to $C_5$ alkinoxy, $C_1$ to $C_5$ alkylthio, $C_2$ to $C_5$ alkenyl-thio or $C_2$ to $C_5$ alkinyl-thio group or a $C_1$ to $C_5$ alkoxy group which is straight-chain or branched and optionally substituted by fluorine, chlorine, bromine, iodine, $C_1$ to $C_5$ alkoxy and/or $C_1$ to $C_5$ alkylthio, or represents a radical of the general formula

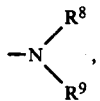

wherein $R^8$ and $R^9$ independently of each other represent a phenyl radical which is optionally substituted by fluorine, bromine, and/or iodine, or represent a straight-chain or branched $C_1$ to $C_5$ alkyl, $C_2$ to $C_5$ alkenyl or $C_2$ to $C_5$ alkinyl group, or wherein $R^8$ and $R^9$, together with the nitrogen atom to which they are bonded, represent a pyrrolidyl radical which is optionally substituted by methyl and/or ethyl, represent a morpholinyl radical which is optionally substituted by methyl, or represent an azacycloheptyl, piperidyl, 3-methyl-piperidyl, 4-methyl-piperidyl, 2-ethyl-piperidyl, 4-ethyl-piperidyl, 2,3-dimethyl-piperidyl, 2,4-dimethyl-piperidyl, 2,5-dimethyl-piperidyl, or 3,5-dimethyl-piperidyl radical.

2. A compound according to claim 1, in which $X^1$ and $X^2$ independently of each other represent a hydrogen or chlorine atom, Y represents a hydrogen or chlorine atom or a cyano or nitro group, m is 0, 1, 2 or 3, n is 0 or 1, p is 0, 1, 2 or 3, $X^3$ and $X^4$ independently of each other represent oxygen or a —CO—O— group, $R^1$, $R^2$, $R^3$ and $R^4$ independently of one another represent a hydrogen atom or a methyl or ethyl group, $R^5$ and $R^6$ independently of each other represent a methyl, ethyl, n-propyl, iso-propyl, n-, iso-, sec.- or tert.-butyl group, and $R^7$ represents a methyl, ethyl, n-propyl, iso-propyl, n-, iso-, sec.- or tert.-butyl or hydroxyl group, a chlorine atom or a methoxy, ethoxy, n-propoxy, iso-propoxy, n-butoxy, iso-butoxy, sec.-butoxy, tert.-butoxy, methylthio, ethylthio, propenoxy, propinoxy, propenylthio or propinylthio group which is optionally substituted by fluorine, chlorine, methoxy, ethoxy, methylthio and/or ethylthio or represents a radical of the general formula

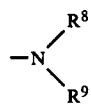

wherein $R^8$ and $R^9$ independently of each other represent an optionally fluorine-substituted and/or chlorine-substituted phenyl, methyl, ethyl, n-propyl, iso-propyl, n-, iso-, sec.- or tert.-butyl, prop-2-enyl, but-2-enyl, prop-2-inyl or but-2-inyl group or wherein $R^8$ and $R^9$, together with the nitrogen atom to which they are bonded, represent a pyrrolidyl radical which is optionally substituted by methyl and/or ethyl, or represent a morpholinyl radical which is optionally substituted by methyl, or represent an aza-cycloheptyl, piperidyl, 3-methyl-piperidyl, 4-methylpiperidyl, 2-ethyl-piperidyl, 4-ethyl-piperidyl, 2,3-dimethylpiperidyl, 2,4-dimethyl-piperidyl, 2,5-dimethyl-piperidyl or 3,5-dimethylpiperidyl radical.

3. A compound according to claim 1, wherein $X^1$ is chlorine.

4. A compound according to claim 3, wherein Y is a 4-nitro group.

5. A compound according to claim 4, wherein $X^2$ is hydrogen.

6. A compound according to claim 4, wherein $X^2$ is chlorine.

7. A compound according to claim 5, of the formula

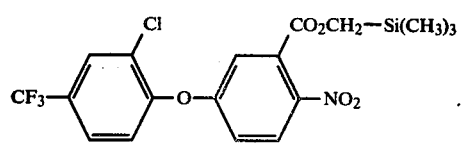

8. A compound according to claim 5, of the formula

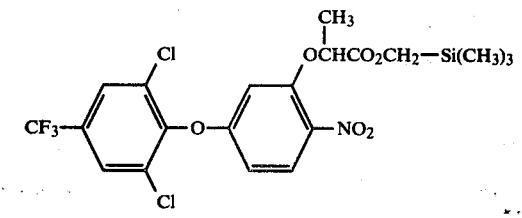

9. A compound according to claim 1, of the formula

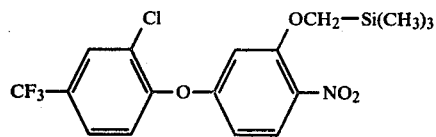

10. A compound according to claim 6, of the formula

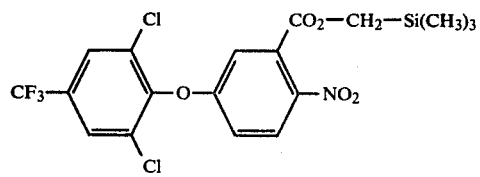

11. A compound according to claim 1, of the formula

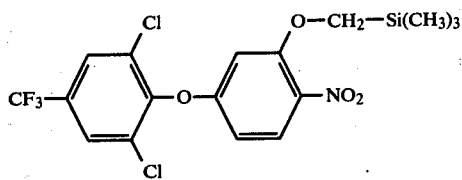

12. A herbicidal or plant growth regulating composition comprising a herbicidally effective amount or plant growth regulatingly effective amount of a compound of claim 1.

13. A composition according to claim 12, wherein the compound of claim 1 is present in an amount of 0.1 to 95 percent by weight.

14. A method of combating weeds which comprises applying to the weeds or to the habitat thereof, a compound according to claim 1 in a herbicidally effective amount.

15. A method of regulating the growth of plants which comprises applying to the plants, or to the habitat thereof, a plant growth regulatingly effective amount of the compound of claim 1.

16. A method according to claim 14, wherein the compound of claim 1 is applied to an area of agriculture in an amount of 0.01 to 50 kg per hectare.

17. A method according to claim 15, wherein the compound according to claim 1, is applied to an area of agriculture in an amount of 0.01 to 50 kg per hectare.

* * * * *

UNITED STATES PATENT AND TRADEMARK OFFICE
CERTIFICATE OF CORRECTION

PATENT NO. : 4,481,365

DATED : November 6, 1984

INVENTOR(S) : Heinz Forster et al

It is certified that error appears in the above-identified patent and that said Letters Patent is hereby corrected as shown below:

| | |
|---|---|
| Abstract, lines 10, 11 and 12 Col. 1, lines 35, 36 and 37; Col. 2, lines 35, 51 and 63; Col. 3, lines 10, 25 and 26; Col. 4, lines 5, 6 and 7; Col. 10, line 46; Col. 16, line 19; Col. 20, line 60; Col. 28, lines 60, 61, 62 and Col. 29, lines 39, 40, 41 | Delete "n", "m" and "p" and substitute --$\underline{n}$--, --$\underline{m}$--, and --$\underline{p}$-- |
| Col. 2, line 3 | Correct spelling of "azacycloheptyl" |
| Col. 4, Table 1, line 2 under "R" | Delete "$CH_3$" and substitute --$N(CH_3)_2$-- |
| Col. 5, last line under "$X^2$" | Delete "Cl" and substitute --H-- |
| Col. 8, line 30 under "R" | Delete "-iso-$C_3H_7$" and substitute -- -O-iso-$C_3H_7$-- |
| Col. 13, line 43 | Delete "m" and substitute --$\underline{m}$-- and --$\underline{n}$-- |
| Col. 13, Table 3 | Fourth line under "$X^3$" insert --$CO_2$--; under "$X^4$" delete "$NO_2$"; under "Y" insert --$NO_2$--; under "$R^2$" delete "O"; under "n" insert --O--. |
| Col. 13, Table 3 | 10th line under "$R^2$" delete "O"; 10th line under "n" insert --O--. |
| Col. 14, line 22 | Delete "p" and substitute --$\underline{p}$-- |

UNITED STATES PATENT AND TRADEMARK OFFICE
CERTIFICATE OF CORRECTION

PATENT NO. : 4,481,365
DATED : November 6, 1984
INVENTOR(S) : Heinz Forster et al It is certified that error appears in the above-identified patent and that said Letters Patent is hereby corrected as shown below:

| | |
|---|---|
| Col. 14, line 30 | Insert --(V)-- next to formula |
| Col. 17, Table 5 | Line 12 under "$R^7$" delete formula and substitute 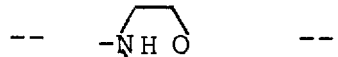 |
| Col. 17, Table 5 | Line 13 under "$R^7$" delete formula and substitute 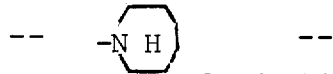 |
| Col. 17, Table 5 | Delete entire 19th line under heading as it is a repetition of line 18 |
| Col. 22, Table 6 | Line 8 under "$R^9$" delete "$CH-CH-CH_2$" and substitute --$CH-CH=CH_2$-- |
| Col. 22, Table 6 | Line 25 under "$R^9$" delete formula and substitute  |
| | Line 25 under "p" insert --1-- |
| Col. 26, line 24 | Correct spelling of "diazabicycloundecene" |

UNITED STATES PATENT AND TRADEMARK OFFICE
CERTIFICATE OF CORRECTION

PATENT NO. : 4,481,365

DATED : November 6, 1984

INVENTOR(S) : Heinz Forster et al

It is certified that error appears in the above-identified patent and that said Letters Patent is hereby corrected as shown below:

Col. 27, line 46            After "15" delete "m" and substitute --cm--

Signed and Sealed this

Ninth Day of April 1985

[SEAL]

*Attest:*

DONALD J. QUIGG

*Attesting Officer*      *Acting Commissioner of Patents and Trademarks*